United States Patent
Ackermann et al.

(10) Patent No.: US 10,403,423 B2
(45) Date of Patent: Sep. 3, 2019

(54) SUPERCONDUCTING MAGNET SYSTEM INCLUDING THERMALLY EFFICIENT RIDE-THROUGH SYSTEM AND METHOD OF COOLING SUPERCONDUCTING MAGNET SYSTEM

(71) Applicant: KONINKLIJKE PHILIPS N.V., Eindhoven (NL)

(72) Inventors: Robert Adolph Ackermann, Eindhoven (NL); Glen George Pfleiderer, Eindhoven (NL); Philip Alexander Jonas, Eindhoven (NL); Matthew Voss, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 485 days.

(21) Appl. No.: 15/034,567

(22) PCT Filed: Oct. 22, 2014

(86) PCT No.: PCT/IB2014/065526
§ 371 (c)(1),
(2) Date: May 5, 2016

(87) PCT Pub. No.: WO2015/071795
PCT Pub. Date: May 21, 2015

(65) Prior Publication Data
US 2016/0276082 A1     Sep. 22, 2016

Related U.S. Application Data

(60) Provisional application No. 61/903,591, filed on Nov. 13, 2013.

(51) Int. Cl.
F25B 9/00      (2006.01)
F25B 9/02      (2006.01)
(Continued)

(52) U.S. Cl.
CPC ............. *H01F 6/04* (2013.01); *A61B 5/0555* (2013.01); *F25B 9/10* (2013.01); *F25D 19/006* (2013.01);
(Continued)

(58) Field of Classification Search
CPC .......... H01F 6/04; F04B 37/08; F04B 37/085; B01D 8/00; F25B 9/00; F25B 9/02;
(Continued)

(56) References Cited

U.S. PATENT DOCUMENTS 5,485,730 A   1/1996  Herd
5,701,742 A  12/1997  Eckels et al.
(Continued)

*Primary Examiner* — Frantz F Jules
*Assistant Examiner* — Erik Mendoza-Wilkenfel

(57) ABSTRACT

A superconducting magnet system, including a cryostat, and a ride-through system for the superconducting magnet system include: one or more gravity-fed cooling tubes configured to have therein a cryogenic fluid; a first heat exchanger configured to transfer heat from the one or more gravity-fed cooling tubes to a cryocooler; a storage device having an input connected to the first heat exchanger and configured to receive and store a boiled-off gas from the first heat exchanger; and a thermal regenerator having an input connected to the output of the storage device.

19 Claims, 3 Drawing Sheets

(51) Int. Cl.

| | | |
|---|---|---|
| *F25B 9/10* | (2006.01) | |
| *F25B 19/00* | (2006.01) | |
| *H01F 6/04* | (2006.01) | |
| *G01R 33/38* | (2006.01) | |
| *A61B 5/055* | (2006.01) | |
| *H01F 6/02* | (2006.01) | |
| *H01F 6/06* | (2006.01) | |
| *F25D 19/00* | (2006.01) | |
| *G01R 33/3815* | (2006.01) | |

(52) U.S. Cl.
CPC .......... *G01R 33/3804* (2013.01); *H01F 6/02* (2013.01); *H01F 6/06* (2013.01); *G01R 33/3815* (2013.01)

(58) Field of Classification Search
CPC ...... F25B 9/04; F25B 9/06; F25B 9/10; F25B 9/12; F25B 9/14; F25B 9/145; F25B 15/006; F25B 15/008; F25B 19/00; F25B 19/005; F25B 19/006
See application file for complete search history.

(56) References Cited

U.S. PATENT DOCUMENTS

| | | | |
|---|---|---|---|
| 6,011,456 A | 1/2000 | Eckels et al. | |
| 8,544,281 B2 | 10/2013 | Zhang et al. | |
| 2002/0063616 A1 | 5/2002 | Ying | |
| 2004/0185305 A1 | 9/2004 | Nemoto et al. | |
| 2005/0062473 A1 | 3/2005 | Ryan | |
| 2007/0101742 A1* | 5/2007 | Laskaris | G01R 33/3804 62/259.2 |
| 2008/0155995 A1 | 7/2008 | Hughes et al. | |
| 2008/0209919 A1* | 9/2008 | Ackermann | F25B 25/005 62/51.1 |
| 2008/0242974 A1* | 10/2008 | Urbahn | F25B 9/14 600/420 |
| 2010/0031693 A1* | 2/2010 | Yuyama | F25D 19/006 62/430 |
| 2012/0094840 A1* | 4/2012 | Tanaka | H01F 6/006 505/211 |
| 2012/0108433 A1 | 5/2012 | Jiang et al. | |
| 2012/0196753 A1 | 8/2012 | Laskaris et al. | |
| 2013/0023418 A1 | 1/2013 | Ackermann et al. | |
| 2014/0243205 A1 | 8/2014 | Ackermann et al. | |

* cited by examiner

300

┌─────────────────────────────────────────────┐
│ Transfer heat from a superconducting magnet │
│ to a first cryogenic fluid disposed within  │─ 310
│ one or more gravity-fed cooling tubes       │
└─────────────────────────────────────────────┘

┌─────────────────────────────────────────────┐
│ Transfer heat from the gravity-fed cooling tube(s) │
│ to a cryocooler via a heat exchanger with a │─ 320
│ volume of a second cryogenic fluid,         │
│ including a cryogenic liquid, disposed therein │
└─────────────────────────────────────────────┘

┌─────────────────────────────────────────────┐
│ Provide boiled-off gas from the heat exchanger │
│ to a storage device configured to store     │─ 330
│ at least some of the boiled-off gas therein │
└─────────────────────────────────────────────┘

┌─────────────────────────────────────────────┐
│ Transfer heat from the storage device       │─ 340
│ to the first stage of the cryocooler        │
└─────────────────────────────────────────────┘

┌─────────────────────────────────────────────┐
│ Supply boiled-off gas from the storage device │─ 350
│ to a thermal regenerator                    │
└─────────────────────────────────────────────┘

FIG. 3

SUPERCONDUCTING MAGNET SYSTEM INCLUDING THERMALLY EFFICIENT RIDE-THROUGH SYSTEM AND METHOD OF COOLING SUPERCONDUCTING MAGNET SYSTEM

CROSS REFERENCE TO RELATED APPLICATIONS

This application is a U.S. national phase application of International Application No. PCT/IB2014/065526, filed on Oct. 22, 2014, which claims the benefit of U.S. Provisional Application Ser. No. 61/903,591 filed on Nov. 13, 2013 and is incorporated herein by reference.

TECHNICAL FIELD

The present invention generally pertains to superconducting magnet systems and cryostats for superconducting magnet systems. In particular, the present invention is related to a ride-through system for cooling a superconducting magnet system, a superconducting magnet system which includes such a ride-through system, and a method of cooling a superconducting magnet system.

BACKGROUND AND SUMMARY

Superconducting magnets are used in a variety of contexts, including nuclear magnetic resonance (NMR) analysis, and magnetic resonance imaging (MRI). To realize superconductivity, the superconducting magnet is maintained in a cryogenic environment at a temperature near absolute zero. Typically, the superconducting magnet includes one or more electrically conductive coils which are disposed in a cryostat containing a substantial volume of a cryogenic fluid such as liquid helium. Many such superconducting magnets operate in "persistent mode." A superconducting magnet which operates in persistent mode is initially energized with current from an external power supply to start up its magnetic field, and then the power supply is disconnected from the superconducting magnet and the superconducting magnet maintains the current and the magnetic field due to its superconductivity.

Although a continuous supply of power is typically not required for the superconducting magnet to sustain the magnetic field, power (e.g., AC Mains power) is still supplied to a compressor which drives a cooling unit or "cold head"—herein referred to as a "cryocooler"—in order to maintain the temperature of the superconducting magnet near absolute zero so that the magnet's superconductivity persist.

Unfortunately, it is possible that the power to the cryocooler may be lost, for example, during an electrical power outage due to a storm. Furthermore, from time to time, the cryocooler may experience some malfunction or need to be turned off to perform maintenance.

When the cryocooler ceases to operate, conditions within the cryostat can degrade and the temperature of the superconducting magnet may begin to rise. At a certain point, if operation of the cryocooler is not reestablished to restore cooling of the superconducting magnet's environment, then the superconducting magnet's temperature will rise to reach a critical temperature where the superconducting magnet will "quench" and convert its magnetic energy to heat energy, thereby heating the cryogenic fluid within the cryostat. This will cause some or all of the cryogenic fluid to evaporate and be lost. Furthermore, the heat may damage the magnet and/or other components of the apparatus.

In that case, once operation of the cryocooler is reestablished, to return the magnet to superconducting operation may require replacing lost cryogenic fluid within the cryostat, cooling the magnet back down to below the critical temperature, connecting leads to the magnet to reapply current from an external power supply to the magnet so as to regenerate the magnetic field, and disconnecting the magnet for the external power supply again. Furthermore, if heat from the quench caused the magnet or other components to be damaged, they may need to be repaired or replaced.

This recovery process can be expensive and time-consuming. Typically, a trained technician must be dispatched to the facility (e.g., a medical center or hospital) where the superconducting magnet system is located and new cryogenic fluid (e.g. liquid helium), which may be quite costly, must be supplied to the cryostat. Further, supplies of helium are becoming increasingly limited and so the cost of lost helium can significant.

Although this can be a significant problem in a typical superconducting magnet system for an MRI apparatus, the problem can be at least somewhat ameliorated by the fact that such superconducting magnet systems typically employ a relatively large volume of cryogenic fluid (e.g., 1000 liters of liquid helium). The large volume of cryogenic fluid has a large thermal mass which may mean that power must be lost for a relatively long time—maybe even days—before the temperature of the magnet reaches the critical temperature and produces a quench. Furthermore, such systems typically have an access means by which a user may add cryogenic fluid to the cryostat from time to time to replace lost of evaporated cryogenic material.

However, some newer MRI apparatuses are being developed and deployed which employ so-called "cryofree" superconducting magnet systems which are closed or sealed and which may not include means for a user to add new cryogenic material to the system. Furthermore, such closed systems typically have a much smaller volume of cryogenic material in their cryostats than the conventional systems described above (e.g., only one liter, or a few liters, of liquid helium).

Accordingly, a quench in a cryofree or sealed superconducting magnet system may occur in only 30 minutes or less after the cryocooler suffers a loss of electrical power or some malfunction, or undergoes maintenance, which prevents it from operating properly and maintaining the temperature in the cryostat to be near absolute zero. Furthermore, since no means is typically provided for a user to add new cryogenic material to the system, if the cryogenic fluid is degraded or evaporated due to a quench, then recovery may require days or weeks.

One aspect of the present invention can provide an apparatus including: one or more gravity-fed cooling tubes configured to have therein a first cryogenic fluid for cooling a superconducting magnet; a first heat exchanger configured to transfer heat from the one or more gravity-fed cooling tubes to a second stage element of a cryocooler, wherein the first heat exchanger is configured to store therein a volume of a second cryogenic fluid; a storage device having an input connected to the first heat exchanger and configured to receive and store a boiled-off gas from the first heat exchanger when the cryocooler stops operating; and a second heat exchanger configured to transfer heat from the storage device to a first stage element of the cryocooler.

In some embodiments, the apparatus further includes an enclosure, and a thermal shield disposed within the enclosure, the thermal shield defining an inner region, and further defining a vacuum space between the thermal shield and a wall of the enclosure, wherein the one or more gravity-fed cooling tubes, the first heat exchanger, the storage device, and the second heat exchanger are disposed within the inner region.

In some versions of these embodiments, the apparatus further includes a thermal regenerator having an input connected to the output of the storage device and having an output connected to an outside of the enclosure In some versions of these embodiments, the thermal regenerator is at least partially disposed in the vacuum space between the thermal shield and the wall of the enclosure.

In some versions of these embodiments, the apparatus further includes a second storage device disposed outside the enclosure and connected to the output of the thermal regenerator.

In some embodiments, the apparatus further includes a cold plate configured to transfer heat from the second heat exchanger to the first stage element of the cryocooler.

In some versions of these embodiments, the apparatus further includes a persistent current switch connected across the superconducting magnet; and at least one high temperature superconducting electrical lead having a first end connected to the superconducting magnet and having a second end connected to the cold plate.

In some embodiments, the storage device has a capacity for storing at least 3 liters of the boiled-off gas.

In some embodiments, the first stage element of the cryocooler is configured to operate at a first temperature and the second stage element of the cryocooler is configured to operate at a second temperature which is less than the first temperature, and the apparatus further includes a thermal switch which is configured to transfer heat from the first heat exchanger to the first stage element of the cryocooler when the first heat exchanger has a temperature which is greater than the first temperature, and which is configured to prevent a transfer of heat from the first stage element of the cryocooler to the first heat exchanger when the temperature of the first heat exchanger is less than the first temperature.

Another aspect of the invention can provide an apparatus including: one or more gravity-fed cooling tubes configured to have disposed therein a first cryogenic fluid for cooling a superconducting magnet; and a heat exchanger configured to have stored therein a volume of a second cryogenic fluid including a cryogenic liquid, wherein the heat exchanger is configured to transfer heat from the one or more gravity-fed cooling tubes to a cryocooler.

In some embodiments, the apparatus further includes a storage device having an input connected to the heat exchanger and configured to receive and store a boiled-off gas from the heat exchanger.

In some versions of these embodiments, the apparatus further includes a thermal regenerator having an input connected to the output of the storage device.

In some versions of these embodiments, the gravity-fed cooling tubes, the heat exchanger, and the storage device are disposed within an enclosure, and the thermal regenerator has an output that is connected to an exterior of the enclosure.

In some versions of these embodiments, the apparatus further includes a second storage device disposed outside the enclosure and connected to the output of the thermal regenerator.

In some versions of these embodiments, the cryocooler has at least a first stage element which is configured to operate at a first temperature and a second stage element which is configured to operate at a second temperature which is less than the first temperature, and the apparatus further includes a second heat exchanger configured to transfer heat from the storage device to the first stage element of the cryocooler, wherein the heat exchanger is configured to transfer heat from the one or more gravity-fed cooling tubes to the second stage element of the cryocooler.

In some embodiments, the cryocooler has at least a first stage element which is configured to operate at a first temperature, and the apparatus further includes a thermal switch configured to transfer heat from the heat exchanger to the first stage element of the cryocooler when the heat exchanger has a temperature which is greater than the first temperature, and which is configured to prevent a transfer of heat from the first stage element of the cryocooler to the heat exchanger when the temperature of the heat exchanger is less than the first temperature.

Yet another aspect of the invention can provide a method including: transferring heat from a superconducting magnet to a first cryogenic fluid disposed within one or more gravity-fed cooling tubes; and transferring heat from the first cryogenic fluid in the one or more gravity-fed cooling tubes to a cryocooler via a heat exchanger which has a second cryogenic fluid, including a cryogenic liquid, disposed therein.

In some embodiments, the method further includes providing a boiled-off gas from the heat exchanger to a storage device configured to store at least some of the boiled-off gas therein.

In some versions of these embodiments, the cryocooler has at least a first stage element which is configured to operate at a first temperature and a second stage element which is configured to operate at a second temperature which is less than the first temperature, and the heat exchanger transfers heat from the one or more gravity-fed cooling tubes to the second stage element of the cryocooler, and the method further includes transferring heat from the storage device to the first stage element of the cryocooler.

In some versions of these embodiments, the method further includes supplying at least some of the boiled-off gas from the storage device to a thermal regenerator.

BRIEF DESCRIPTION OF THE DRAWINGS

The present invention will be more readily understood from the detailed description of exemplary embodiments presented below considered in conjunction with the accompanying drawings.

FIG. 3 illustrates some operations of an example embodiment of a method of cooling a superconducting magnet.

DETAILED DESCRIPTION

The present invention will now be described more fully hereinafter with reference to the accompanying drawings, in which embodiments of the present invention are shown. The present invention may, however, be embodied in different forms and should not be construed as limited to the embodiments set forth herein. Rather, these embodiments are provided as teaching examples of the invention. Within the present disclosure and claims, when something is said to have approximately a certain value, then it means that it is within 10% of that value, and when something is said to have about a certain value, then it means that it is within 25% of that value. When something is said to be substantially greater, then it means that it is at least 10% greater, and when something is said to be substantially less, then it means that it is at least 10% less.

Figure 1:
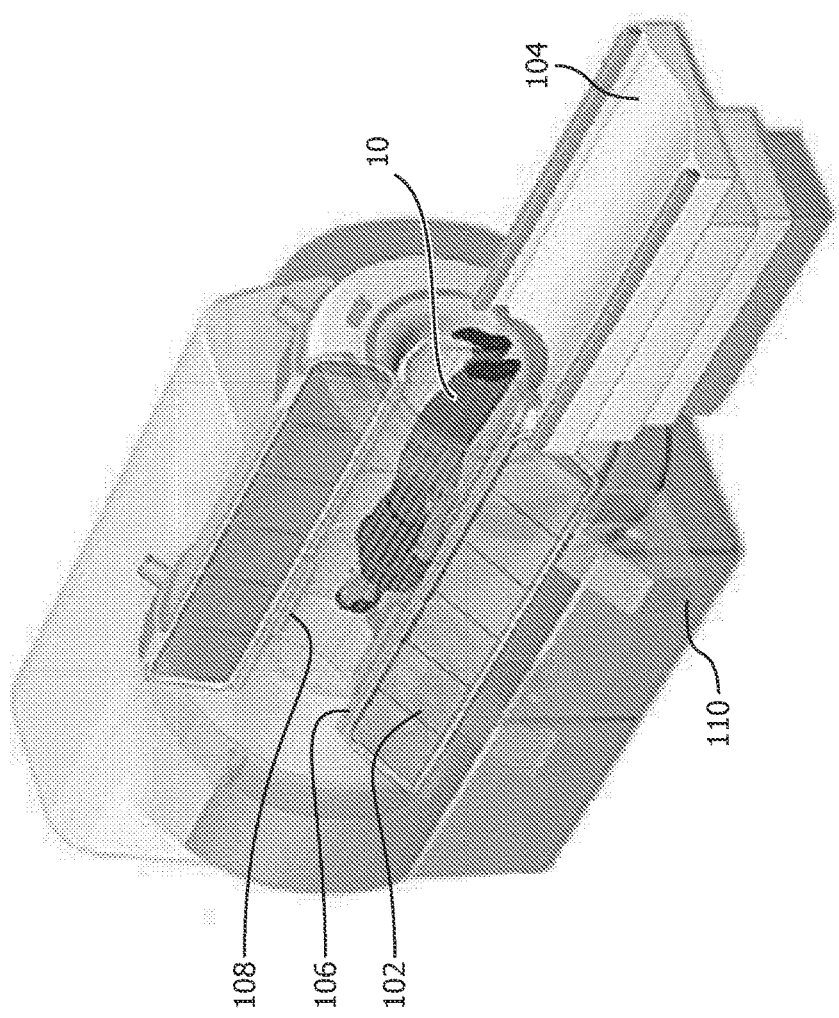
FIG. 1 illustrates an exemplary embodiment of a magnetic resonance (MR) imager.

FIG. 1 illustrates an exemplary embodiment of a magnetic resonance imaging (MRI) apparatus 100. MRI apparatus 100 may include a magnet 102; a patient table 104 configured to hold a patient 10; gradient coils 106 configured to at least partially surround at least a portion of patient 10 for which MRI apparatus 100 generates an image; a radio frequency coil 108 configured to apply a radio frequency signal to at least the portion of patient 10 which is being imaged, and to alter the alignment of the magnetic field; and a scanner 110 configured to detect changes in the magnetic field caused by the radio frequency signal.

The general operation of an MRI apparatus is well known and therefore will not be repeated here.

Figure 2:
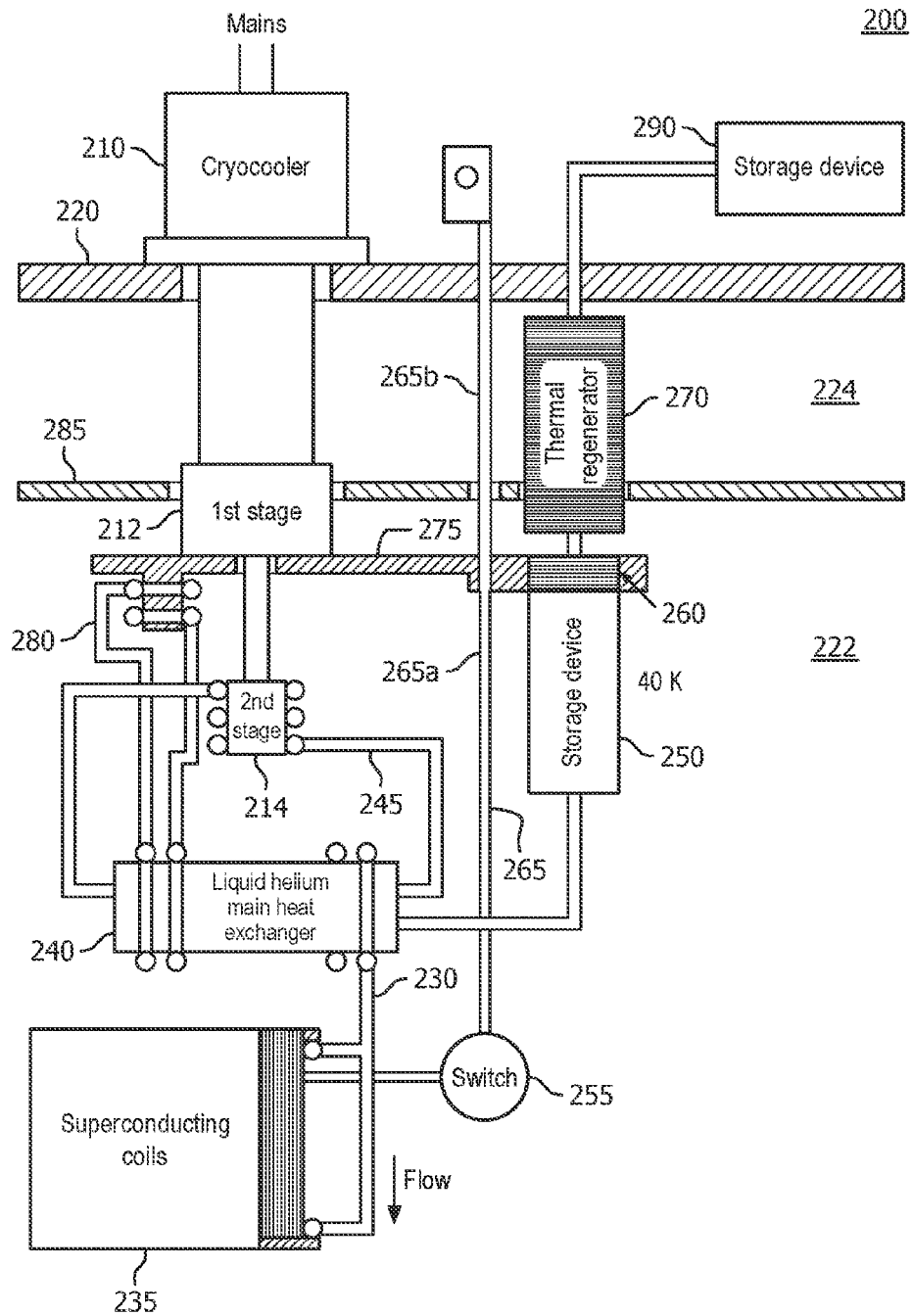
FIG. 2 illustrates one embodiment of a superconducting magnet system including a ride-through system for riding through a cryocooler malfunction for an extended period without quenching a magnetic field generated by a superconducting magnet.

FIG. 2 illustrates one embodiment of a superconducting magnet system 200 including a ride-through system for riding through a cryocooler malfunction for an extended period without quenching a magnetic field generated by a superconducting magnet. In particular, superconducting magnet system 200 may be one embodiment of magnet 102 in MRI apparatus 100.

Superconducting magnet system 200 includes cryocooler 210 and a housing or enclosure 220 defining a cryostat.

In some embodiments, cryocooler 210 may include a Gifford-McMahon (GM) cooler. As illustrated in FIG. 2, in some embodiments cryocooler may be configured to be connected to AC main to receive electrical power for its operation. In other embodiments, an external power supply or power conditioning unit may instead supply electrical power to cryocooler 210.

Cryocooler 210 can include a first stage element 212 and a second stage element 214. In the embodiment illustrated in FIG. 2, cryocooler 210 includes two stages, but in other embodiments it is possible for cryocooler 210 to have a different number of stages other than two.

Superconducting magnet system 200 also includes one or more gravity-fed cooling tubes 230, a first heat exchanger 240, a first storage device 250, a second heat exchanger 260, a thermal regenerator 270, a thermal switch 280, and a second storage device 290. Superconducting magnet system 200 further includes a superconducting magnet 235 including one or more electrically conductive coils, a cooling loop 245, a persistent current switch 255, one or more high temperature superconducting electrical leads 265, a cold plate 275, and a thermal shield 285.

Gravity-fed cooling loop(s) 230 is/are configured in operation to have a first cryogenic fluid (e.g., cold gaseous helium) disposed and circulating therein. Gravity-fed cooling loop(s) 230 is/are thermally connected (directly or indirectly) at a lower end thereof to the or more electrically conductive coils of superconducting magnet 235, and connected at an upper end thereof to first heat exchanger 240.

First heat exchanger 240 is configured to have a second cryogenic fluid disposed therein. In some embodiments, the second cryogenic fluid includes a volume of liquid helium, and may further include a volume or cold gaseous helium.

First heat exchanger 240 is thermally connected via cooling loop 245 to second stage element 214 of cryocooler 210.

First storage device (or storage tank) 250 has an inlet/input connected to first heat exchanger 240, and as explained in greater detail below, is configured to receive and store a boiled-off gas from first heat exchanger 240 when the cryocooler 210 stops operating. In some embodiments, first storage device 250 has a capacity for storing at least 3 liters of boiled-off gas (e.g., helium gas) from first heat exchanger 240. In some embodiments, first storage device 250 has a capacity for storing at least 5 liters of boiled-off gas from first heat exchanger 240. In some embodiments, first storage device 250 may have a capacity for storing up to 30 liters of boiled-off gas from first heat exchanger 240.

Thermal shield 285 substantially encompasses an inner region 222 within enclosure 220, and further defines an outer region 224 which is disposed between enclosure 220 and thermal shield 285. Each of the inner region 222 and the outer region 224 may be a vacuum region.

In superconducting magnet system 200, the one or more gravity-fed cooling tubes 230, first heat exchanger 240, first storage device 250, second heat exchanger 260, thermal switch 280, superconducting magnet 235, cooling loop 245, persistent current switch 255, and cold plate 275 are disposed in inner region 222. Some or all of thermal regenerator 270 may be disposed in outer region 224.

Persistent current switch 255 may include a piece of superconductor wire connected across opposite ends of the electrically conductive coil(s) of superconducting magnet 235 and attached to a small persistent current switch heater.

High temperature superconducting electrical lead(s) 265 connect an external power supply (not shown in FIG. 2) to persistent current switch 255 and superconducting magnet 235 during a startup operation of superconducting magnet 235 as explained in greater detail below. High temperature superconducting electrical lead(s) 265 may be made of a material which experiences superconductivity at a relatively high temperature, for example, at a temperature greater than 40° K, and in particular, at or around 77° K. Each of the high temperature superconducting electrical lead(s) 265 may include a lower portion 265a and an upper portion 265b. The upper portion of electrical lead(s) 265 may be comprised of a non-super conducting material such as copper. In particular, lower portion 265a is disposed within inner region 222, and some or all of upper portion 265b is disposed within outer region 224.

Second heat exchanger 260 is disposed at or near a top portion and outlet/output of first storage device 250. Second heat exchanger 260 is configured to transfer heat from first storage device 250 to first stage element 212 of cryocooler 210. In the illustrated embodiment, second heat exchanger 260 conveys heat from first storage device 250 to first stage element 212 of cryocooler 210 via cold plate 275, which for example may be at a temperature of about 40 degrees Kelvin during normal operation. Also, in the illustrated embodiment, second heat exchanger 260 conveys heat from high temperature superconducting lead(s) 265 to first stage element 212 of cryocooler 210 via cold plate 275 so as to maintain the temperature of high temperature superconducting lead(s) 265 before its critical temperature, for example below 60 degrees Kelvin.

Thermal regenerator 270 has a high volumetric heat capacity and a low thermal conductivity in the longitudinal (flow) direction from the input (bottom) to the output (top) thereof. In some embodiments, thermal regenerator 270 may be constructed of a matrix material that has the capability of quickly transferring and storing heat from a gas which passes through, but which is also highly resistant to heat flowing along its longitudinal direction. In some embodiments, as compared to a counter-flow heat exchanger, thermal generator 270 does not require a simultaneous continuous flow of two physically separated fluids, but instead transfers heat to and from the same gas (e.g., helium gas) by the action of the intermediate heat transfer with the regenerator material each time the gas direction is cyclically reversed. To accomplish this, the hotter gas may be brought into contact with the heat storage medium or matrix of thermal regenerator 270, then the warmer gas is displaced with the colder gas, which absorbs the heat. Thermal regenerator 270 has an input connected to the output of first storage device 250 and has an output connected to an outside of enclosure 220. In the illustrated embodiment, thermal regenerator 270 is disposed in whole or in part in second region 224 between thermal shield 285 and enclosure 220.

Thermal switch 280 is connected between first heat exchanger 240 at its lower end, and first stage element 212 of cryocooler 210 and cold plate 285 at its upper end. In some embodiments, thermal switch 280 is a convective cooling loop which is configured to allow heat to flow from its lower end to its upper end, but to prevent heat from flowing from its upper end to its lower end.

In the illustrated embodiment, second storage device 290 is disposed exterior to, or on an outside of enclosure 220. Accordingly, second storage device 290 may assume a room temperature (e.g. 300 degrees Kelvin) of a room or facility where superconducting magnet system 200 is installed. In some embodiments, second storage device 290 has a capacity for storing about 40 liters or more of boiled-off gas (e.g., helium gas) from first heat exchanger 240, received via first storage device 250 and thermal regenerator 270. In some embodiments, second storage device 290 has a capacity for storing at least 100 liters of boiled-off gas from first heat exchanger 240. In some embodiments, second storage device 290 has a capacity for storing at least 300 liters of boiled-off gas from first heat exchanger 240. In some embodiments, second storage device 290 may have a capacity for storing up to 500 liters of boiled-off gas from first heat exchanger 240.

Exemplary operations of superconducting magnet system 200 will now be described.

During a startup operation of superconducting magnet system 200, the wire in persistent current switch 255 is heated by a small persistent current switch heater above its transition temperature, so that it becomes resistive. High temperature superconducting lead(s) 265 connect an external power supply (not shown in FIG. 2) to persistent current switch 255 and superconducting magnet 235 during a startup operation of superconducting magnet 235. The electrically conductive coil(s) of superconducting magnet 235 are initially energized by the external power supply passing a current therethrough. Since the wire in persistent current switch 255 is being heated during the startup operation, its resistance is substantially greater than that of the electrically conductive coil(s) of superconducting magnet 235, so the current from the external power supply passes through the electrically conductive coil(s) of superconducting magnet 235.

Meanwhile, first stage element 212 of cryocooler 210 operates at a first temperature (e.g., about 40 degrees Kelvin) and second stage element 214 operates at a second temperature (e.g., about 4 degrees Kelvin) which is lower than the first temperature. The one or more gravity-fed cooling tubes 230 contain therein a first cryogenic fluid, for example, super-cold gaseous helium at about 4 to 5 degrees Kelvin. First heat exchanger 240 stores a volume (e.g. one liter) of a second cryogenic fluid, including, for example, liquid helium at about 4 degrees Kelvin.

Accordingly, cryocooler 210 is able to provide refrigeration to cool the electrically conductive coils of superconducting magnet 235 below their superconducting temperature (e.g., at or below 4.2 degrees Kelvin) by means of the one or more gravity-fed cooling tubes 230 and first heat exchanger 240. Cryocooler 210 is further able to provide refrigeration (e.g., at about 40 degrees Kelvin) to maintain high temperature superconducting lead(s) 265 below its/ their transition temperature (e.g., about 60 degrees Kelvin) via cold plate 275 and second heat exchanger 260.

The super-cold helium gas circulating in one or more gravity-fed cooling tubes 230 is cooled by the evaporation of a second cryogenic fluid (e.g., liquid helium), which is contained in first heat exchanger 240. In turn, the evaporated helium vapor from first heat exchanger 240 is condensed by second stage element 214 of cryocooler and liquid helium is returned to first heat exchanger 240 via cooling loop 245.

Since, as described above, the electrically conductive coil(s) of superconducting magnet 235 are cooled by gravity-fed cooling tubes 230 to below its critical temperature, the electrically conductive coil(s) of superconducting magnet 235 are superconducting.

To go to persistent mode, the current through the electrically conductive coil(s) of superconducting magnet 235 is adjusted until the desired magnetic field is obtained, then the heater in persistent current switch 255 is turned off. After the heater is turned off, the superconductor wire in persistent current switch 255 cools to its superconducting temperature, short-circuiting the electrically conductive coil(s) of superconducting magnet 235, which as mentioned above, are also superconducting. In some embodiments, at this point high temperature superconducting lead(s) 265 may be disconnected from persistent current switch 255 and the electrically conductive coil(s) of superconducting magnet 235. At this point, superconducting magnet 235 may operate in persistent mode.

During normal operation, cryocooler 210 continues to cool the electrically conductive coils of superconducting magnet 235 to maintain their superconductivity (e.g., at a temperature of about 4 degrees Kelvin) via second stage element 214 and gravity-fed cooling tubes 230, and also cools high temperature superconducting electrical lead(s) 265 to maintain their superconductivity (e.g., at a temperature of about 40 degrees Kelvin) via first stage element 212, cold plate 275, and second heat exchanger 260. Also during normal operation, the temperature of first heat exchanger 240 (e.g., about 4 degrees Kelvin) is substantially less than the operating temperature of first stage element 212 and cold plate 275 (e.g., about 40 degrees Kelvin), but because first heat exchanger 240 is located below first stage element 212 and cold plate 275, thermal switch 280 prevents a transfer of heat from first stage element 212 of cryocooler 210 to first heat exchanger 240.

If cryocooler 210 stops operating for any reason, such as a loss of electrical power, a malfunction, or for routine maintenance, then a loss of cooling will occur, and if no additional refrigeration is provided, both the electrically conductive coils of superconducting magnet 235, and high temperature superconducting electrical lead(s) 265, will start to warm with the potential of quenching the magnet.

To prevent a quench, superconducting magnet system 200 includes a ride-through system. The ride-through system of superconducting magnet system 200 may be considered to include first heat exchanger 240, first storage device 250, second heat exchanger 260, thermal regenerator 270, and second storage device 290. However, in other embodiments one or more of these elements may be omitted, for example, the first storage device 250, second heat exchanger 260, thermal regenerator 270, and/or second storage device 290, with perhaps an attendant loss of some benefits and/or reduction in performance.

If cryocooler 210 does not operate properly to cool second stage element 214, then some of the cryogenic fluid (e.g., liquid helium) stored in first heat exchanger 240 may boil off. In that case, first storage device 250 has its input connected to first heat exchanger 240 and is configured to receive and store the boiled-off gas from first heat exchanger 240 when cryocooler 210 stops operating. As first storage device 250 fills with the boiled-off gas, and as the temperature of the boiled-off gas rises, some of the boiled-off gas may exit first storage device 250 from an output thereof which is thermally connected via second heat exchanger 260 to cold plate 285, which may normally operate at about 40 degrees Kelvin. The cool gas departing first storage device 250 is provided to thermal regenerator 270, whose operation has been explained above. Warmer gas leaves thermal regenerator 270 and exits enclosure 220 to be provided to second storage device 290. Meanwhile, if the temperature of first heat exchanger 240 should start to rise above the temperature of first stage element 212 of cryocooler 210 and cold plate 285 (for example, about 60 degrees Kelvin), then thermal switch 280 allows heat to be transferred from first heat exchanger 240 to first stage element 212 of cryocooler 210 and cold plate 285.

The ride-through system may include one or more of the storage volumes shown in FIG. 2 to provide sufficient ride-through time while limiting the pressure rise within components of superconducting magnet system 200. Superconducting magnet system 200 includes three storage volumes, including a first storage volume in first heat exchanger 240 at 4 degrees Kelvin, a second or intermediate storage volume in first storage device 250 at 40 degrees Kelvin, and a third storage volume in second storage device 290 at room temperature (e.g., at 300° K) disposed outside of enclosure 220. Thermal regenerator 270 disposed between first storage device 250 at 40 degrees Kelvin and second storage device 290 at room temperature (e.g., at 300° K) may allow cooling to be transferred from the cold flow of gas (e.g., helium) exiting enclosure 220 to a warm gas re-entering enclosure 220 after proper operation of cryocooler 210 resumes. The multiple volumes give the ride-through system the flexibility to collect a ride-through gas without exceeding the safe working pressure of components in superconducting magnet system 200 when it is initially charged with gas (e.g., helium) at room temperature. This also achieves the objective of having a system that is hermetically sealed and does not requires additional cryogenic material (e.g., helium) to be added to the system. However, as explained above, in some embodiments one or more of these storage volumes may be omitted, perhaps with an attendant loss of some benefits and/or reduction in performance.

In some embodiments, these volumes may be sized to limit the temperature rise in the electrically conductive coils of superconducting magnet 235 to less than their critical quench temperature, for example by limiting the pressure rise of the helium vapor in the volumes. In some embodiments, as long as the pressure in first heat exchanger 240 does not rise above a pressure threshold (e.g., 1.64 atm at 4.8 degrees Kelvin), and the upper portion 265b of high temperature superconducting electrical lead(s) 265 does not exceed 60 degrees Kelvin, then the electrically conductive coils of superconducting magnet 235 and high temperature superconducting electrical lead(s) 265 will not quench and the system will operate normally.

The ride-through system of superconducting magnet system 200 may store sufficient cryogenic fluid (e.g., helium liquid and/or super-cooled helium gas) during normal operation to provide cooling to both electrically conductive coils of superconducting magnet 235 and high temperature superconducting electrical lead(s) 265 for an extended period of time when cryocooler 210 is not operating. The ride-through system may also enable a relatively quick recovery of cooling and restoration of superconducting magnet system 200 to its normal operating mode once cryocooler 210 resumes normal operation.

In some embodiments, in the event that cryocooler 210 ceases to operate properly, the ride-through system may be able to maintain the electrically conductive coils of superconducting magnet 235 below 4.9 degrees Kelvin and the upper portion 265b of high temperature superconducting electrical lead(s) 265 below about 60 degrees Kelvin for an extended time period, for example, more than two hours and beneficially, at least four hours.

In various embodiments, superconducting magnet system 200 and its ride-through system may prevent or delay the occurrence of a magnet quench during routine cryocooler maintenance or failure of cryocooler 210. Furthermore, having multiple volumes of cryogenic fluids at different temperatures may maintain a safe working pressure of the system while minimizing the size of volumes. In some embodiments, the presence of second heat exchanger 260 near high temperature superconducting lead(s) 265 allows the use of the cold helium vapor leaving first heat exchanger 240 via storage device 250 to keep the superconducting lead(s) 265 below its/their critical temperature. Furthermore, in some embodiments, thermal regenerator 270 can enable most or all of refrigeration in the evaporated cryogenic fluid (e.g., cold helium gas) to be stored and returned to the gas efficiently once normal operation of cryocooler 220 is reestablished. Storing the refrigeration in thermal regenerator 270, rather than dissipating it, may enable liquid helium to be returned to first heat exchanger 240 with a minimum of cooling required from cryocooler 220 once normal operation of cryocooler 220 is reestablished. In some cases, thermal regenerator 270 may allow normal operation of superconducting magnet system 200 to resume in a matter of hours after normal operation of cryocooler 220 is reestablished, while it may require days to return a superconducting magnet system to its normal operating mode without thermal regenerator 270.

FIG. 3 illustrates some operations of an example embodiment of a method 300 of cooling a superconducting magnet. In some embodiments, the operations of method 300 may be performed by superconducting magnet system 200 of FIG. 2.

Method 300 can include an operation 310 of transferring heat from a superconducting magnet (e.g., element 235 in FIG. 2) to a first cryogenic fluid disposed in one or more gravity-fed cooling tubes (e.g., element 230 in FIG. 2), so as to cool the superconducting magnet. In some embodiments, the first cryogenic fluid is in a gaseous state, for example cold gaseous helium. The cold helium gas is provided to the superconducting magnet disposed at the bottom of the gravity-fed cooling tube(s), and as heat is transferred from the superconducting magnet to the cold helium gas, the temperature of the cold helium gas increases. The "warmer" helium gas causes an increase in pressure within the cooling tube(s) which circulates the warmer helium gas, which was heated by the superconducting magnet, to the top of the gravity-fed cooling tube(s), and in turn sends the colder helium gas to the bottom of the gravity-fed cooling tube(s) where it can absorb heat from the superconducting magnet.

Method 300 also can include an operation 320 of transferring heat from the first cryogenic fluid in the one or more gravity-fed cooling tubes to a cryocooler (e.g., element 210 in FIG. 2) via a heat exchanger (e.g., element 240 in FIG. 2) which has a volume of a second cryogenic fluid, including a cryogenic liquid (e.g., liquid helium), disposed therein. In some embodiments, the heat exchanger is disposed at the top of the gravity-fed cooling tube(s), and the warmer helium gas, which was heated by the superconducting magnet, circulates to the top of the gravity-fed cooling tube(s) where it exchanges heat with the second cryogenic fluid which is disposed in the heat exchanger. The transfer of heat from the gaseous helium to the volume of a second cryogenic fluid in the heat exchanger decreases the temperature and pressure of the gaseous helium, which then circulates back to the bottom of the gravity-fed cooling tube(s) to absorb more heat from the superconducting magnet, as described in operation 310 above.

The second cryogenic fluid, which is heated by the gaseous helium of the gravity-fed cooling tube(s), in turn transfers its heat to the cryocooler. In some embodiments, the cryocooler has at least a first stage element (e.g., element 212 in FIG. 2) which is configured to operate at a first temperature (e.g., about 40° K) and a second stage element (e.g., element 214 in FIG. 2) which is configured to operate at a second temperature (e.g., about 4° K) which is less than the first temperature, and the heat exchanger transfers the heat from the one or more gravity-fed cooling tubes to the second stage element of the cryocooler. In some embodiments, the heat is transferred from the heat exchanger to the second stage element of the cryocooler via a cooling loop (e.g., element 245 in FIG. 2).

As noted above, in some cases cryocooler 210 may stop operating properly for any of a variety of reasons, such as a loss of electrical power, a malfunction, or for routine maintenance. In that case, then some of the cryogenic fluid (e.g., liquid helium) stored in the heat exchanger may boil off.

Accordingly, method 300 can include an operation 330 of providing a boiled-off gas from the heat exchanger to a storage device (e.g., element 250 in FIG. 2) which is configured to store at least some of the boiled-off gas therein. This may increase the time period during which the superconducting magnet system may be able to ride through a loss of cooling by the cryocooler without experiencing a magnet quench.

To further delay or prevent a magnet quench, method 300 can include an operation 340 of transferring heat from the storage device to the first stage of the cryocooler, as described above with respect to superconducting magnet system 200 of FIG. 2.

Furthermore, to shorten a time period which is required for reestablishing normal operations of the superconducting magnet system after the cryocooler has ceased operation, method 300 can include an operation 350 of supplying at least some of the boiled-off gas from the storage device to a thermal regenerator, as described above with respect to superconducting magnet system 200 of FIG. 2.

In other embodiments, a method of cooling a superconducting magnet may include one or more various other operations which have been described above with respect to superconducting magnet system 200 and FIG. 2.

While preferred embodiments are disclosed herein, many variations are possible which remain within the concept and scope of the invention. Such variations would become clear to one of ordinary skill in the art after inspection of the specification, drawings and claims herein. The present invention therefore is not to be restricted except within the scope of the appended claims.

What is claimed is:

1. An apparatus comprising:
   one or more gravity-fed cooling tubes configured to have therein a first cryogenic fluid for cooling a superconducting magnet;
   a first heat exchanger configured to transfer heat from the one or more gravity-fed cooling tubes to a second stage element of a cryocooler, wherein the first heat exchanger is configured to store therein a volume of a second cryogenic fluid that cools the first cryogenic fluid;
   a storage device having an input connected to the first heat exchanger and configured to receive and store a boiled-off gas from the second cryogenic fluid stored in the first heat exchanger when the cryocooler stops operating;
   a second heat exchanger configured to transfer heat from the storage device to a first stage element of the cryocooler; and
   a thermal regenerator having an input connected to an output of the storage device.

2. The apparatus of claim 1, further comprising:
   an enclosure; and
   a thermal shield disposed within the enclosure, the thermal shield defining an inner region, and further defining a vacuum space between the thermal shield and a wall of the enclosure, wherein the one or more gravity-fed cooling tubes, the first heat exchanger, the storage device, and the second heat exchanger are disposed within the inner region.

3. The apparatus of claim 2, wherein the thermal regenerator comprises a matrix material, and the thermal regenerator has an output connected to an outside of the enclosure.

4. The apparatus of claim 3, wherein the thermal regenerator is at least partially disposed in the vacuum space between the thermal shield and the wall of the enclosure.

5. The apparatus of claim 3, further comprising a second storage device disposed outside the enclosure and connected to the output of the thermal regenerator.

6. The apparatus of claim 1, further comprising a cold plate configured to transfer heat from the second heat exchanger to the first stage element of the cryocooler.

7. The apparatus of claim 6, further comprising:
   a persistent current switch connected across the superconducting magnet; and
   at least one high temperature superconducting electrical lead having a first end connected to the superconducting magnet and having a second end connected to the cold plate.

8. The apparatus of claim 1, wherein the storage device has a capacity for storing at least 3 liters of the boiled-off gas.

9. The apparatus of claim 1, wherein the first stage element of the cryocooler is configured to operate at a first temperature and the second stage element of the cryocooler is configured to operate at a second temperature which is less than the first temperature, the apparatus further comprising a thermal switch which is configured to transfer heat from the first heat exchanger to the first stage element of the cryocooler when the first heat exchanger has a temperature which is greater than the first temperature, and which is configured to prevent a transfer of heat from the first stage element of the cryocooler to the first heat exchanger when the temperature of the first heat exchanger is less than the first temperature.

10. An apparatus, comprising:
    one or more gravity-fed cooling tubes configured to have disposed therein a first cryogenic fluid for cooling a superconducting magnet;
    a heat exchanger configured to have stored therein a volume of a second cryogenic fluid including a cryogenic liquid, wherein the heat exchanger is configured to transfer heat from the one or more gravity-fed cooling tubes to a cryocooler, and wherein the second cryogenic fluid is physically isolated to be separate from the first cryogenic fluid;
    a storage device having an input connected to the heat exchanger and configured to receive and store a boiled-off gas from the second cryogenic fluid stored in the heat exchanger; and
    a thermal regenerator having an input connected to an output of the storage device.

11. The apparatus of claim 10, wherein the gravity-fed cooling tubes, the heat exchanger, and the storage device are disposed within an enclosure, and wherein the thermal regenerator has an output that is connected to an exterior of the enclosure.

12. The apparatus of claim 11, further comprising a second storage device disposed outside the enclosure and connected to the output of the thermal regenerator.

13. The apparatus of claim 10, wherein the cryocooler has at least a first stage element which is configured to operate at a first temperature and a second stage element which is configured to operate at a second temperature which is less than the first temperature, the apparatus further comprising a second heat exchanger configured to transfer heat from the storage device to the first stage element of the cryocooler, wherein the heat exchanger is configured to transfer heat from the one or more gravity-fed cooling tubes to the second stage element of the cryocooler.

14. The apparatus of claim 10, wherein the cryocooler has at least a first stage element which is configured to operate at a first temperature, the apparatus further comprising a thermal switch configured to transfer heat from the heat exchanger to the first stage element of the cryocooler when the heat exchanger has a temperature which is greater than the first temperature, and which is configured to prevent a transfer of heat from the first stage element of the cryocooler to the heat exchanger when the temperature of the heat exchanger is less than the first temperature.

15. A method, comprising:
    transferring heat from a superconducting magnet to a first cryogenic fluid disposed within one or more gravity-fed cooling tubes;
    transferring heat from the first cryogenic fluid in the one or more gravity-fed cooling tubes to a cryocooler via a heat exchanger which has a second cryogenic fluid, including a cryogenic liquid, disposed therein, wherein the second cryogenic fluid is physically isolated to be separate from the first cryogenic fluid;
    providing a boiled-off gas from the second cryogenic fluid stored in the heat exchanger to a storage device configured to store at least some of the boiled-off gas therein; and
    supplying at least some of the boiled-off gas from the storage device to a thermal regenerator.

16. The method of claim 15, wherein the cryocooler has at least a first stage element which is configured to operate at a first temperature and a second stage element which is configured to operate at a second temperature which is less than the first temperature, wherein the heat exchanger transfers heat from the one or more gravity-fed cooling tubes to the second stage element of the cryocooler, the method further comprising transferring heat from the storage device to the first stage element of the cryocooler.

17. The apparatus of claim 10 wherein the thermal regenerator comprises a matrix material that resists heat flow along a longitudinal direction of the thermal regenerator.

18. The apparatus of claim 10 wherein the thermal regenerator comprises a heat storage material.

19. The apparatus of claim 10 wherein the thermal regenerator comprises a heat storage material that resists heat flow along a longitudinal direction of the thermal regenerator.

* * * * *